United States Patent [19]

Chow et al.

[11] Patent Number: 4,883,785

[45] Date of Patent: Nov. 28, 1989

[54] COMPLEX OF ANTI-FUNGAL AGENT AND CYCLODEXTRIN AND METHOD

[76] Inventors: Wing-Sun Chow, 26 Marquette Rd., Upper Montclair, N.J. 07043; Shirley C. Chen, 91 George Ave., Edison, N.J. 08820; Peter Timmins, 34, Thornley Road, Morton, Wirral, Merseyside, United Kingdom, L46 6HB

[21] Appl. No.: 635,030

[22] Filed: Jul. 27, 1984

[51] Int. Cl.⁴ .................... A61K 31/70; C07H 17/08
[52] U.S. Cl. ........................................ 514/31; 514/58; 536/6.5; 536/46; 536/112
[58] Field of Search .............. 424/361, 180; 536/6.5, 536/46, 112; 514/31, 58

[56] References Cited

U.S. PATENT DOCUMENTS

| | | |
|---|---|---|
| 4,383,992 | 5/1983 | Lipari . |
| 4,423,040 | 12/1983 | Rajadhyaksha ............... 424/180 |
| 4,438,106 | 3/1984 | Wagu et al. .................. 536/103 |
| 4,482,709 | 11/1984 | Iwao et al. ................... 536/46 |
| 4,497,803 | 2/1985 | Harada et al. ................ 536/7.1 |

FOREIGN PATENT DOCUMENTS 56-122332 9/1981 Japan .

OTHER PUBLICATIONS

Saenger, W., "Cyclodextrin Inclusion Compounds in Research and Industry," Angew. Chem. Int. Ed. Engl., 19, 344-362, (1980).

Uekama et al., "Enhanced Bioavailability of Acetohexamide by α-Cyclodextrin Complexation," Yakugaku Zasshi, vol. 100, 1980, pp. 903-909.

Cserhali et al., "Effect of Water-Soluble β-Cyclodextrin Polymer on the Lipophilicity of Polymyxin Examined by Reversed Phase Thin-Layer Chromatography", Journal of Chromatography, 259, (1983), 107-110, Elsevier.

*Primary Examiner*—Johnnie R. Brown
*Assistant Examiner*—Elli Peselev
*Attorney, Agent, or Firm*—Burton Rodney

[57] ABSTRACT

An anti-fungal complex formed of a polyene anti-fungal agent, such as amphotericin B, and cyclodextrin, preferably γ-cyclodextrin, is provided. The complex which includes amphoterin B has improved water solutility and stability over prior art amphotericin B anti-fungal agents. A method for forming the complex is also provided wherein anti-fungal agent, such as amphoterin B, is dissolved in an aqueous solution of cyclodextrin of pH ranging from about 9 to about 12 and the resulting solution is maintained at a pH ranging from about 6 to about 8 to form the subject complex. The solution can be lyophilized as desired to achieve higher solubility.

7 Claims, No Drawings

COMPLEX OF ANTI-FUNGAL AGENT AND CYCLODEXTRIN AND METHOD

FIELD OF THE INVENTION

The present invention relates to an anti-fungal complex having improved water-solubility and stability which is formed from a polyene anti-fungal agent, such as, amphotericin B, and cyclodextrin, and to methods of forming such complex.

BACKGROUND OF THE INVENTION

Cyclodextrins are cyclic oligosaccharides obtained from starch, formed of six glucose units (α-cyclodextrin), seven glucose units (β-cyclodextrin) or eight glucose units (γ-cyclodextrin). They are known to form inclusion compounds with smaller molecules which fit entirely or at least partially into the 5-8 A cyclodextrin cavity, Saenger, W.,"Cyclodextrin Inclusion Compounds in Research and Industry," Angew. Chem. Int. Ed. Engl. 19, 344-362 (1980). At page 351, Saenger indicates that α-cyclodextrin forms complexes with water, methanol, polyiodide, iodine, krypton, n-propanol, p-iodoaniline, dimethyl sulfoxide and methanol, m-nitrophenol, methyl orange, prostaglandin E, potassium acetate; β-cyclodextrin forms complexes with water, n-propanol, p-iodophenol, 2,5-diiodobenzoic acid, p-nitoacetanilide; and γ-cyclodextrin forms complexes with propanol/water and water.

In addition, Saenger indicates at page 357 that β-cyclodextrin increases stabilization of benzocaine, procaine, atropine, aspirin, nitroglycerin, allicin, phenylbutazone, salicylic acid, ascaridole, the ethyl ester of chaulmoogric acid, linoleic acid and indomethacin, and cyclodextrins increase water-solubility of fatty acids, amines such as procaine, lidocaine, meperdine, adipherine, steroids such as cortisone acetate and testosterone, hydroxybenzoic acids, benzocaine, aspirin, p-aminobenzoic acid, tetracycline, sulfadiazine, morphine, vanillin, ephedrine, sorbic acid, phenyl-substituted carbonic acids, ketoprofen, other antipyretic agents, vitamin $D_3$, coumarin anticoagulants, sulfonamides and barbiturates.

U. S. Pat. No. 4,383,992 to Lipari discloses water-soluble complexes of β-cyclodextrin with various steroids having a molecular structure smaller than the interior cavity in the doughnut-shaped molecular structure of β-cyclodextrin, such as corticosteroids, androgens, anabolic steroids, estrogens and progestagens. The Lipari patent indicates that these complexes are useful in aqueous topical ophthalmic preparations and topical dermatological ointments.

Uekame et al, "Enhanced Bioavailability of Acetohexamide by β-Cyclodextrin Complexation," Yakugaku Zasshi, Vol. 100, 1980, pp. 903-909 discloses an inclusion complex of acetohexamide with β-cyclodextrin.

Japanese Kokai Pat. No. Sho 56 [1981]-122332 discloses a gefarnate clathrate in which a gefarnate is clathrated with cyclodextrin.

Cserhali et al,"Effect of Water-Soluble β-Cyclodextrin Polymer on the Lipophilicity of Polymyxin Examined by Reversed Phase Thin-Layer Chromatography", Journal of Chromatography, 259 (1983) 107-110, Elsevier, discloses that the water-soluble β-cyclodextrin polymer forms inclusion complexes with the antibiotic polymyxin.

Amphotericin B is a potent antifungal agent but which has poor water-solubility and stability. Accordingly, an amphotericin B compound or formation which has improved water-solubility and stability would be a most welcomed addition to the anti-fungal field.

DESCRIPTION OF THE INVENTION

In accordance with the present invention, a new anti-fungal complex or inclusion compound is provided which is formed of an anti-fungal agent, such as a polyene anti-fungal agent, preferably amphotericin B, and a cyclodextrin.

In addition, in accordance with the present invention, there is provided a new water-soluble stable form of amphotericin B which comprises a complex or inclusion compound of a cyclodextrin with amphotericin B. It has been found that the amphotericin B-cyclodextrin complex has a water-solubility and stability which are substantially greater than that of known amphotericin B compounds or formulations. Furthermore, the complex of the invention has improved palatability, light stability and toxicity over known amphotericin B compounds or formulations.

Examples of polyene anti-fungal agents suitable for use herein include, but are not limited to, amphotericin B, candicidin, hamycin, pimaricin and other known natural and semi-synthetic polyene anti-fungal agents, with amphotericin B being preferred.

The cyclodextrin employed in the complex with the polyene ant-fungal agent, such as amphotericin B, may be β-cyclodextrin or γ-cyclodextrin, with γ-cyclodextrin being preferred.

In general, the complex of the invention will include a molar ratio of anti-fungal agent to cyclodextrin of within the range of from about 1:20 to about 1:100, preferably from about 1:30 to about 1:70, and optimally from about 1:40 to about 1:60.

The complex of anti-fungal agent and a cyclodextrin may be formed by forming an aqueous solution of the cyclodextrin containing from about 1 to about 5% by weight cyclodextrin and adding anti-fungal agent in an amount to provide a weight ratio of anti-fungal agent to cyclodextrin of from about 1:2 to about 1:65, with stirring until the anti-fungal agent is dissolved and a solution of the complex is formed.

In a preferred method, in accordance with the present invention, the complex of the invention is formed by forming an aqueous solution of the cyclodextrin having a cyclodextrin concentration of within the range of from about 1 to about 5% by weight, and preferably from about 2 to about 3.5% by weight, and having a pH within the range of from about 9 to about 12, the pH being adjusted, as is necessary, using strong base such as an alkali metal hydroxide, for example, NaOH, KOH or LiOH, adding anti-fungal agent, such as amphotericin B, to the cyclodextrin solution to provide a weight ratio of anti-fungal agent to cyclodextrin of within the range of from about 1:2 to about 1:65, and preferably from about 1:40 to about 1:65, with agitation, while maintaining the reaction at a temperature within the range of from about 5 to about 15° C., and adjusting the pH of the resulting solution to within the range of from about 6 to about 8 using strong acid, such as $H_3PO_4$, HCl, $H_2SO_4$ or HF, to form a solution of complex of anti-fungal agent and cyclodextrin. In an optional step, the pH of 6 to 8 of the solution may be maintained by the addition thereto of buffering agent such as K or Na phosphate, K or Na citrate, K or Na tartrate, Na maleate, Na₂CO₃, NaHCO₃ and the like. Due to the increased stability of the resulting formulation, this addition can be brought to room temperature without loss of potency. Thereafter, the solution may be filtered using a 0.2 to 2 micron filter, if desired, and the filtered solution of the complex recovered.

In the above method of the invention, it is important that the pH of the solution of cyclodextrin in water be maintained at within the range of from about 9 to 12 before anti-fungal agent, such as amphotericin B addition to ensure that the subsequently added anti-fungal agent remains in solution. In the case of amphotericin B as the anti-fungal agent, the pH of the amphotericin B and cyclodextrin mixture will be maintained at from about 6 to about 8 to ensure that the amphotericin B will be included as a guest molecule into the host cyclodextrin molecule and thereby form a complex with cyclodextrin.

In an alternative embodiment, a mixture of amphotericin B and cyclodextrin in the form of a paste is kneaded and then the mass is dried to form the complex.

The so-formed complex of the invention may be orally administered in solution form or formulated as solid dosage forms, suppositories (rectal and vagina) or the complex may be incorporated in semi-solid type of formulations or in enema formulations. To form a solid dosage form, the solution of complex may be freeze dried (lyophilized) or solid recovered from solution by conventional preferential precipitation techniques or by conventional kneading methods. In another method, the solution of complex may be spray dried on to a support substrate such as a non-toxic substrate, such as carboxymethyl cellulose, hydrogels or cellulose or lactose, for oral use, or on a water-soluble substrate such as sorbitol, mannitol, sucrose, arginine or phospholipid and reconstituted with water or other conventional diluents or additives to form liquid formulations.

Solution form of the complex of the invention is particularly effective when administered orally to combat upper gastrointestinal infections, such as of the esophagus and stomach. Solid formulations administered orally are effective in combatting infections of the stomach and intestines. Enema and suppository formulations are effective in combatting lower gastrointestinal, vaginal and rectal infections. Semi-solid formulations are effective in topical infections.

The preferred complex of amphotericin B and cyclodextrin of the invention has been found to have reduced toxicity, improved water-solubility and stability over prior art amphotericin B compounds and/or formulations and thus is easily dissolved in the stomach, even at the acidic pH of 1–1.5 normally found in the stomach. In addition, the complex of the invention is found to be substantially less susceptible to photo-degradation and more palatable than prior art amphotericin B compounds and/or formulations.

The following Examples represent preferred embodiments of the present invention. All temperatures are expressed in degrees Centigrade unless otherwise indicated.

EXAMPLE 1

A complex formed of γ-cyclodextrin and amphotericin B, in accordance with the present invention, was prepared as described below.

A solution of 0.1 ml of 1N sodium hydroxide and 2.7 ml distilled water was chilled to 7° C. with a wet ice bath. Thereafter 77.8 mg (0.06 mmole) of crystalline γ-cyclodextrin was added slowly with agitation and the mix was stirred for about 3 minutes until the γ-cyclodextrin was completely dissolved. A solution of γ-cyclodextrin was thereby formed having a pH of 12.6.

Amphotericin B (30 mg, 0.03 mmole) was added in increments to the γ-cyclodextrin solution with vigorous stirring over a 15 minute period. The mix was stirred for an additional 10 minutes to dissolve the amphotericin B. Vigorous stirring was continued and the temperature of the solution was maintained at 5°–10° C. while the pH was adjusted to about 8 by adding about 0.43 ml of 1N phosphoric acid solution. The temperature of the solution was then allowed to rise slowly to 20°–25° C.

The so-formed solution was found to contain 26 mg/ml of complex of amphotericin B and γ-cyclodextrin.

The concentration of amphotericin B in the so-formed solution was found to be 1.17 mg (4.24%) out of the starting 30 mg of amphotericin B or 400 μg/ml.

The apparent solubility of this complex of amphotericin B and γ-cyclodextrin in water is 800 fold greater than amphotericin B itself which has a solubility of 0.5 μg/ml.

EXAMPLE 2

A complex formed of γ-cyclodextrin and amphotericin B, in accordance with the present invention, was prepared as described below.

A solution of 0.2 ml of 1N sodium hydroxide and 3.8 ml distilled water was chilled to 7° C. with a wet ice bath. Thereafter 130 mg (0.1 mmole) of crystalline γ-cyclodextrin was added slowly with agitation and the mix was stirred for about 3 minutes until the γ-cyclodextrin was completely dissolved. A solution of γ-cyclodextrin was thereby formed having a pH of 11.5.

Amphotericin B (2 mg, 0.002 mmole) was added in increments to the γ-cyclodextrin solution with vigorous stirring over a 15 minute period. The mix was stirred for an additional 10 minutes to dissolve the amphotericin B. Vigorous stirring was continued and the temperature of the solution was maintained at 5°–10° C. while the pH was adjusted to about 7.5 by adding about 0.43 ml of 1N phosphoric acid solution. The temperature of the resulting solution was then allowed to rise slowly to 20°–25° C. and was buffered with sodium phosphate to maintain pH at 7.5.

The so-formed solution was filtered through a 0.45 micron HA type filter and the filtered solution was found to contain 26 mg/ml of complex of amphotericin B and γ-cyclodextrin and a solubilized amphotericin B concentration of 400 μg/ml.

The solubility of the complex of amphotericin B and γ-cyclodextrin was 800 fold greater than amphotericin B itself. Ninety percent potency was maintained after 7 days of storage at 5°.

EXAMPLE 3

A complex formed of β-cyclodextrin and amphotericin B, in accordance with the present invention, was prepared as described below.

A solution of 0.1 ml of 1N sodium hydroxide and 2.7 ml distilled water was chilled to 7° C. with a wet ice bath. Thereafter 67.22 mg (0.06 mmole) of crystalline β-cyclodextrin was added slowly with agitation and the mix was stirred for about 3 minutes until the β-cyclodextrin was completely dissolved. A solution of β-cyclodextrin was thereby formed having a pH of 12.6.

Amphotericin B (30 mg, 0.03 mmole) was added in increments to the β-cyclodextrin solution with vigorous stirring over a 15 minute period. The mix was stirred for an additional 10 minutes to dissolve the amphotericin B. Vigorous stirring was continued and the temperature of the solution was maintained at 5°-10° C. while the pH was adjusted to about 8 by adding about 0.07ml of 1N phosphoric acid solution. The temperature of the resulting solution was then allowed to rise slowly to 20°-25° C.

The so-formed solution was found to contain 80 μg/ml of amphotericin B.

This solubility of the so-formed complex is 160 fold greater than amphotericin B itself.

EXAMPLE 4

A complex formed of γ-cyclodextrin and amphotericin B, in accordance with the present invention, was prepared as described below.

A solution of 0.2 ml of 1N sodium hydroxide and 3.8 ml distilled water was chilled to 7° C. with a wet ice bath. Thereafter 130 mg (0.1 mmole) of crystalline γ-cyclodextrin was added slowly with agitation and the mix was stirred for about 3 minutes until the γ-cyclodextrin was completely dissolved. A solution of γ-cyclodextrin was thereby formed having a pH of 11.5.

Amphotericin B (2 mg, 0.002 mmole) was added in increments to the γ-cyclodextrin solution with vigorous stirring over a 15 minute period. The mix was stirred for an additional 10 minutes to dissolve the amphotericin B. Vigorous stirring was continued and the temperature of the solution was maintained at 5°-10° C. while the pH was adjusted to about 7.5 by adding about 0.43 ml of 1N phosphoric acid solution. The temperature of the resulting solution was then allowed to rise slowly to 20°-25° C. and was buffered with sodium phosphate to maintain pH at 7.5.

The resulting solution was then lyophilized as follows. Each 10 ml of the solution was placed into 15 cc. glass vials and frozen overnight in a freeze dryer at −50° C. Vacuum was then applied at 250 microns or $3.3 \times 10^{-1}$ m bar. Shelf temperature was raised to 30° C. at a gradually increasing heating rate of 25 to 40% over a 24 hour period. Vacuum was reduced to 50 μ and maintained for 24 hours for secondary drying. The freeze dryer chamber was flooded with nitrogen and the vials stoppered under partial vacuum.

The resulting lyophilized product contains 290 mg of complex of amphotericin B and γ-cyclodextrin and can be solubilized to an amphotericin B concentration of not less than 8 mg/ml representing a 16,000 fold increase of solubility over that of amphotericin B itself.

Full 100% potency was found in the solid lyophilized complex.

This solid lyophilized complex was found to retain 100% potency for more than 8 weeks under room temperature or 40° C. storage.

What is claimed is:

1. An anti-fungal complex having improved water-solubility and stability comprising a polyene anti-fungal agent selected from the group consisting of amphotericin B, candicidin, hamycin, and pimaricin and β- or γ-cyclodextrin in a molar ratio of anti-fungal agent to cyclodextrin of within the range of from about 1:2 to about 1:100.

2. The complex as defined in claim 1 wherein said complex includes a molar ratio of anti-fungal agent to cyclodextrin of within the range of from about 1:2 to about 1:65.

3. The complex as defined in claim 1 wherein said anti-fungal agent is amphotericin B and said cyclodextrin is γ-cyclodextrin.

4. An anti-fungal composition comprising an effective amount of an anti-fungal complex as defined in claim 1 and a pharmaceutically acceptable carrier therefor.

5. The composition as defined in claim 4 in the form of a liquid or semi-solid dosage form.

6. The composition as defined in claim 4 wherein the cyclodextrin is γ-cyclodextrin and the anti-fungal agent is amphotericin B.

7. A complex of amphotericin B with gammacyclodextrin.

* * * * *